(12) United States Patent
Stringer et al.

(10) Patent No.: US 7,541,000 B2
(45) Date of Patent: Jun. 2, 2009

(54) MICRO-PROCESSOR CONTROLLED ACTIVE GAS REMOVAL APPARATUS

(75) Inventors: Steven K. Stringer, Los Gatos, CA (US); Kevin L. Hultquist, Mountain View, CA (US); Mehrdad Farhangnia, Sunnyvale, CA (US); Ben F. Brian, III, Menlo Park, CA (US); Fred I. Linker, Los Altos, CA (US); James M. Culp, Los Gatos, CA (US); Jean-Pierre Dueri, Sunnyvale, CA (US); Thomas A. Afzal, Menlo Park, CA (US)

(73) Assignee: Cardiovention, Inc., Menlo Park, CA (US)

( * ) Notice: Subject to any disclaimer, the term of this patent is extended or adjusted under 35 U.S.C. 154(b) by 0 days.

(21) Appl. No.: 11/236,269

(22) Filed: Sep. 26, 2005

(65) Prior Publication Data

US 2006/0029515 A1    Feb. 9, 2006

Related U.S. Application Data

(63) Continuation of application No. 10/616,116, filed on Jul. 8, 2003, now Pat. No. 6,960,322, which is a continuation of application No. 09/780,923, filed on Feb. 9, 2001, now Pat. No. 6,730,267.

(51) Int. Cl.
*A61M 1/14* (2006.01)
*A61M 37/00* (2006.01)
*C02F 1/44* (2006.01)
*B01D 53/22* (2006.01)
*B01D 47/08* (2006.01)

(52) U.S. Cl. .......................... 422/45; 422/44; 604/4.01; 604/6.09; 604/6.14; 210/645

(58) Field of Classification Search ............. 422/44–48; 604/4.01–6.16, 104–109, 174–175, 264; 210/247, 305, 645; 261/19, 24–30, 35, 34.1, 261/36.1; 128/898; 423/235
See application file for complete search history.

(56) References Cited

U.S. PATENT DOCUMENTS 3,701,433 A    10/1972    Krakauer et al.

(Continued)

OTHER PUBLICATIONS

Matayoshi et al., "Development of a Completely Close Circuit Using an Air Filter in a Drainage Circuit for Minimally Invasive Cardiac Surgery," Artificial Organs 24(6):454-458 (2000).

(Continued)

*Primary Examiner*—Leslie R Deak
*Assistant Examiner*—Phil Wiest
(74) *Attorney, Agent, or Firm*—Jones Day; Nicola A. Pisano, Esq.

(57) ABSTRACT

Apparatus and methods for pumping and oxygenating blood are provided that include a gas removal system. An integrated blood processing unit is provided in which a gas removal/blood filter, pump and blood oxygenation element are mounted within a common housing. The gas removal system includes a sensor mounted on the housing to sense the presence of gas, and a valve is operably coupled to the sensor to evacuate gas from the system when the sensor detects an accumulation of gas.

10 Claims, 8 Drawing Sheets

U.S. PATENT DOCUMENTS

| | | | |
|---|---|---|---|
| 3,827,562 A | | 8/1974 | Esmond |
| 4,056,476 A | | 11/1977 | Mouwen et al. |
| 4,087,363 A | | 5/1978 | Rosenmeyer et al. |
| 4,111,829 A | | 9/1978 | Bimond et al. |
| 4,126,558 A | | 11/1978 | Luceyk |
| 4,157,965 A | * | 6/1979 | Raible .................. 210/305 |
| 4,164,468 A | | 8/1979 | Raible |
| 4,202,760 A | * | 5/1980 | Storey et al. ............. 252/364 |
| 4,280,495 A | | 7/1981 | Lampert |
| 4,283,289 A | * | 8/1981 | Meyst et al. ............. 210/448 |
| 4,319,580 A | | 3/1982 | Colley et al. |
| 4,354,500 A | | 10/1982 | Colley et al. |
| 4,354,501 A | | 10/1982 | Colley et al. |
| 4,354,502 A | | 10/1982 | Colley et al. |
| 4,401,566 A | | 8/1983 | Igari et al. |
| 4,411,783 A | * | 10/1983 | Dickens et al. ........... 210/304 |
| 4,490,254 A | * | 12/1984 | Gordon et al. ............ 210/247 |
| 4,490,331 A | * | 12/1984 | Steg, Jr. .................. 422/46 |
| 4,493,705 A | | 1/1985 | Gordon et al. |
| 4,572,724 A | * | 2/1986 | Rosenberg et al. ............ 96/6 |
| 4,653,577 A | | 3/1987 | Noda |
| 4,662,906 A | | 5/1987 | Matkovich et al. |
| 4,676,771 A | * | 6/1987 | Henke .................. 604/6.09 |
| 4,690,762 A | | 9/1987 | Katsura |
| 4,698,207 A | | 10/1987 | Bringham et al. |
| 4,747,826 A | * | 5/1988 | Sassano .................. 604/522 |
| 4,876,066 A | | 10/1989 | Bringham et al. |
| 4,919,802 A | | 4/1990 | Katsura |
| 4,923,438 A | | 5/1990 | Vasconcellos et al. |
| 4,981,413 A | | 1/1991 | Elonen et al. |
| 5,011,469 A | | 4/1991 | Buckberg et al. |
| 5,017,103 A | | 5/1991 | Dahl |
| 5,055,198 A | | 10/1991 | Shettigar |
| 5,158,533 A | | 10/1992 | Strauss et al. |
| 5,158,534 A | * | 10/1992 | Berry et al. .............. 604/6.14 |
| 5,162,102 A | | 11/1992 | Nogawa et al. |
| 5,188,604 A | | 2/1993 | Orth |
| 5,205,153 A | | 4/1993 | Hlavinka et al. |
| 5,232,437 A | | 8/1993 | Lysaght et al. |
| 5,266,265 A | | 11/1993 | Raible |
| 5,270,005 A | | 12/1993 | Raible |
| 5,334,309 A | | 8/1994 | Huggett et al. |
| 5,394,732 A | | 3/1995 | Johnson et al. |
| 5,411,472 A | | 5/1995 | Steg, Jr. et al. |
| 5,445,613 A | | 8/1995 | Orth |
| 5,503,801 A | | 4/1996 | Brugger |
| 5,514,335 A | | 5/1996 | Leonard et al. |
| 5,591,251 A | | 1/1997 | Brugger |
| 5,591,399 A | * | 1/1997 | Goldman et al. ............... 422/44 |
| 5,632,894 A | | 5/1997 | White et al. |
| 5,634,892 A | | 6/1997 | Whalen |
| 5,651,765 A | * | 7/1997 | Haworth et al. ............ 604/6.09 |
| 5,695,717 A | * | 12/1997 | Polaschegg et al. ........... 422/48 |
| 5,746,575 A | | 5/1998 | Westphal et al. |
| 5,762,684 A | | 6/1998 | Hayashi et al. |
| 5,770,073 A | * | 6/1998 | Bach et al. .................. 210/472 |
| 5,823,986 A | | 10/1998 | Peterson |
| 5,840,068 A | | 11/1998 | Cartledge |
| 5,863,179 A | | 1/1999 | Westphal et al. |
| 5,876,611 A | | 3/1999 | Shettigar |
| 5,899,873 A | | 5/1999 | Jones et al. |
| 5,965,089 A | * | 10/1999 | Jarvik et al. ................... 422/44 |
| 5,997,816 A | | 12/1999 | McIntosh et al. |
| 6,017,493 A | * | 1/2000 | Cambron et al. ............... 422/44 |
| 6,071,258 A | * | 6/2000 | Dalke et al. ................. 604/5.01 |
| 6,206,632 B1 | | 3/2001 | Gallus |
| 6,224,829 B1 | * | 5/2001 | Piplani et al. ................. 422/45 |
| 6,241,945 B1 | * | 6/2001 | Owen .......................... 422/44 |
| 6,267,926 B1 | * | 7/2001 | Reed et al. .................... 422/48 |
| 6,302,860 B1 | | 10/2001 | Gremel et al. |
| 6,315,751 B1 | * | 11/2001 | Cosgrove et al. ........... 604/5.01 |
| 6,328,712 B1 | | 12/2001 | Cartledge |
| 6,337,049 B1 | * | 1/2002 | Tamari ....................... 422/44 |
| 6,503,450 B1 | | 1/2003 | Afzal et al. |
| 6,508,859 B1 | * | 1/2003 | Zia et al. ....................... 95/46 |
| 6,524,267 B1 | | 2/2003 | Gremel et al. |
| 6,730,267 B2 | | 5/2004 | Stringer et al. |
| 7,204,958 B2 | * | 4/2007 | Olsen et al. ................... 422/44 |
| 2004/0195178 A1 | | 10/2004 | Carpenter et al. |
| 2004/0197223 A1 | | 10/2004 | Olsen et al. |
| 2004/0217054 A1 | | 11/2004 | Olsen et al. |
| 2004/0220509 A1 | | 11/2004 | Olsen et al. |

OTHER PUBLICATIONS

Medtronic, "The Bio-Pump Centrifugal Blood Pump." (1998).

Morita et al., "Closed Circuit Cardiopulmonary Bypass with Centrifugal Pump for Open-Heart Surgery: New Trial for Air Removal," Artificial Organs 24(6):442-445 (2000).

Jorge Ojita, et al., "Assisted Venous Drainage Cardiopulmonary Bypass in Congenital Heart Surgery," Ann. Thorac. Surg., 71: 1267-72 (2001).

Joseph J. Sistino et al., "Laboratory Evaluation of a Low Prime Closed Circuit Cardiopulmonary Bypass System," J.Extra-Corp. Tech., 24 (4):116-119 (1993).

Declaration of Jorge Ojito, Aug. 2003.

Declaration of Yehuda Tamari, Sep. 4, 2003.

* cited by examiner

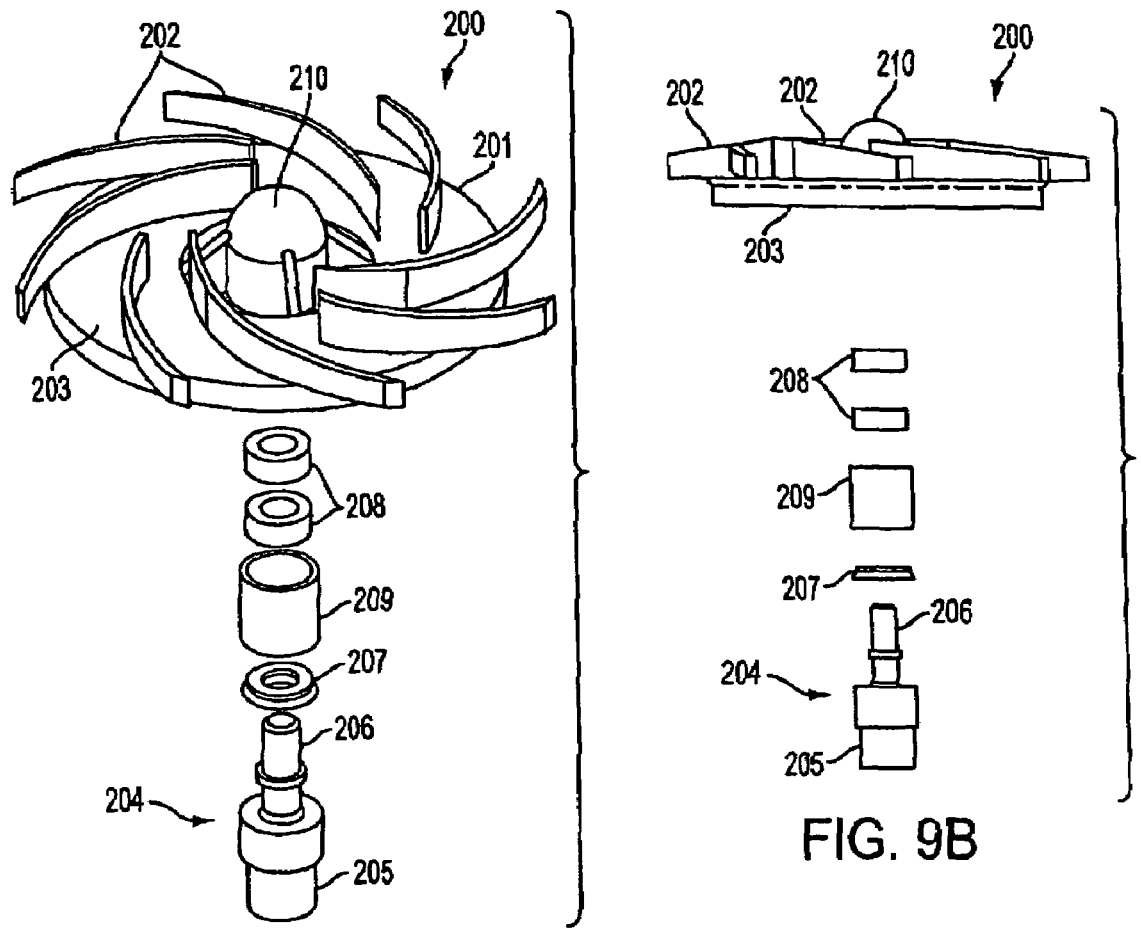
FIG. 9A
FIG. 9B
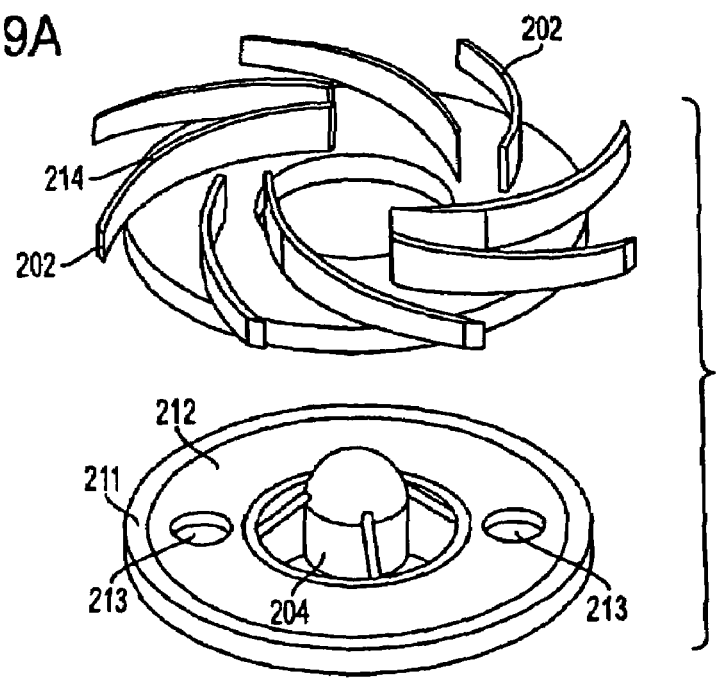
FIG. 10

MICRO-PROCESSOR CONTROLLED ACTIVE GAS REMOVAL APPARATUS

REFERENCE TO RELATED APPLICATIONS

This application is a continuation of application Ser. No. 10/616,116, filed Jul. 8, 2003, which is a continuation of application Ser. No. 09/780,923, filed Feb. 9, 2001.

FIELD OF THE INVENTION

The present invention relates to apparatus and methods for pumping, oxygenating and filtering blood having means for removing air or other gasses from the blood.

BACKGROUND OF THE INVENTION

Each year hundreds of thousands of people are afflicted with vascular diseases, such as arteriosclerosis, that result in cardiac ischemia. For more than thirty years, such disease, especially of the coronary arteries, has been treated using open surgical procedures, such as coronary artery bypass grafting. During such bypass grafting procedures, a sternotomy is performed to gain access to the pericardial sac, the patient is put on cardiopulmonary bypass, and the heart is stopped using a cardioplegia solution.

The development of minimally invasive techniques for cardiac bypass grafting, for example, by Heartport, Inc., Redwood City, Calif. and CardioThoracic Systems, Inc., Menlo Park, Calif. have placed a premium on reducing the size of equipment employed in the sterile field. Whereas open surgical techniques typically provide a relatively large surgical site that the surgeon views directly, minimally invasive techniques require the placement of endoscopes, video monitors, and various positioning systems for the instruments. These devices crowd the sterile field and can limit the surgeon's ability to maneuver.

At the same time, however, the need to reduce priming volume of the oxygenator and pump, and the desire to reduce blood contact with non-native surfaces has increased interest in locating the oxygenator and pump as near as possible to the patient.

In recognition of the foregoing issues, some previously known cardiopulmonary systems have attempted to miniaturize and integrate certain components of cardiopulmonary systems. U.S. Pat. Nos. 5,266,265 and 5,270,005, both to Raible, describe an extracorporeal blood oxygenation system having an integrated blood reservoir, an oxygenator formed from a static array of hollow fibers, a heat exchanger, a pump and a pump motor that is controlled by cable connected to a control console.

One drawback of systems of the type described in foregoing patents, however, arises during priming of the extracorporeal circuit, and in particular, in the need to use large quantities of saline or donor blood to prime the systems. Such fluids are required to flush air out of the system and, because they are relatively incompressible, ensure that the pump used in the extracorporeal circuit develops sufficient pressure head to propel oxygenated blood back to the patient.

In view of this limitation of previously known blood handling systems, it would be desirable to provide a blood handling system and methods that automatically remove air from an extracorporeal blood circuit.

It further would be desirable to blood handling systems and methods that permit one or more additional blood processing components, such as a heat exchanger, to be added to an extracorporeal blood circuit without having to prime the component prior to bringing that component online, thereby reducing disruption to operation of the blood handling system.

It also would be desirable to provide an extracorporeal blood handling system and methods wherein the blood handling system has compact size and low surface area, and reduces contact between the blood and foreign surfaces, thus reducing priming volume, hemolysis and platelet activation.

It still further would be desirable to provide a blood handling system and methods that provide progressive filtration of blood passing through the system, thus reducing the risk that a single blood filter element will become clogged during extended operation.

SUMMARY OF THE INVENTION

In view of the foregoing, it is an object of the present invention to provide apparatus and methods for handling blood that automatically remove air from an extracorporeal blood circuit.

It is another object of the present invention to provide a blood handling system and methods that permit one or more blood processing components, such as a heat exchanger, to be added to an extracorporeal blood circuit without having to prime the component prior to bringing that component online, thereby reducing disruption to operation of the blood handling system.

It is yet another object of this invention to provide an extracorporeal blood handling system and methods wherein the blood handling system has compact size and low surface area, and reduces contact between the blood and foreign surfaces, thus reducing priming volume, hemolysis and platelet activation.

It is a further object of the present invention to provide a blood handling system and methods that provide progressive filtration of blood passing through the system, thus reducing the risk that a single blood filter element will become clogged during extended operation.

These and other objects of the present invention are accomplished by providing a blood handling system comprising an integrated blood oxygenator and pump system having means for removing air or other gases from the extracorporeal blood circuit. In accordance with the principles of the present invention, the blood handling system includes a gas collection plenum, a line adapted to be connected to a suction source, and a sensor that controls coupling of the suction source to the gas collection plenum to selectively remove gas from the blood handling system. The blood handling system of the present invention therefore may be initially primed with little or no saline or donor blood, and with reduced risk of hemodilution.

Moreover, additional components may be added to an existing extracorporeal circuit with little or no additional priming, and any air or other gases introduced into the system will be evacuated with no substantial impact on operation of the blood pump of the blood handling system.

In a preferred embodiment, a blood handling system of the present invention maintains total or partial bypass support for a patient and comprises a housing having a blood inlet, a blood outlet, a gas collection plenum, a blood oxygenation element, a blood pump and a gas removal system.

Blood entering the housing via the blood inlet flows through the gas collection plenum and a first blood filter component that forms part of the gas removal system. Air or other gases entrained in the blood are separated from the blood and collect in the gas collection plenum. A sensor disposed in communication with the gas collection plenum senses a parameter indicative of a level or volume of gas collected in the plenum, and selectively evacuates the plenum by coupling the plenum to a suction source, such as a standard operating room suction port.

Blood exiting the first blood filter component passes to a centrifugal blood pump, which propels the blood through the blood oxygenation element. The blood oxygenation element preferably comprises an annular fiber bundle, e.g., an annular bundle of hollow gas exchange tubes, positioned within the housing. In accordance with another aspect of the present invention, the annular filter bundle serves as a second blood filtration element.

Blood exiting the blood oxygenation element then passes through an additional blood filter element before exiting from the housing through the blood outlet. Blood processed through the system therefore passes through multiple blood filters, which may be progressively finer, distributed throughout the housing, thereby reducing the risk that any one of the filters will be overburdened and clog during extended use of the system.

In still another aspect of the invention, the blood oxygenation element receives blood from the blood pump on a side of the annular fiber bundle that is diametrically opposite to the blood outlet. The inlet to the annular fiber bundle preferably includes an inlet manifold and the blood outlet of the housing preferably has an outlet manifold. The inlet and outlet manifolds preferably extend longitudinally along diametrically opposite sides of the blood oxygenation element, so that blood flows from one side to the diametrically opposite side of the blood oxygenation element.

In a preferred embodiment, the gas removal system includes a gas removal/blood filter element having a cylindrical shape. The gas removal/blood filter comprises a support structure that supports a screen-like material having an effective pore size between 40 and 250 microns. Alternatively, the gas removal/blood filter element may comprise a pleated filter material. Blood is introduced into the gas collection plenum via the blood inlet in a direction substantially tangential to the gas removal/blood filter, to increase residence time of the blood within the gas collection plenum, thereby enhancing separation of entrained gas.

In still another aspect of the present invention, the housing of blood oxygenation element includes at least one relief area positioned radially inward from the annular fiber bundle. More preferably, a relief area is positioned radially inward from each of the inlet and outlet manifolds to permit expansion of the annular fiber bundle at these locations, and to increase the porosity of the fibers in the manifold area and decrease resistance to flow.

Methods of operating the blood handling system of the present invention also are provided.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIGS. 9A and 9B are, respectively, exploded perspective and side views of the impeller, bearing assembly and shaft of the blood pump of the present invention;

FIG. 10 is an exploded perspective view depicting an injection molding process for the impeller of FIGS. 9;

DETAILED DESCRIPTION OF THE INVENTION

Figure 1:
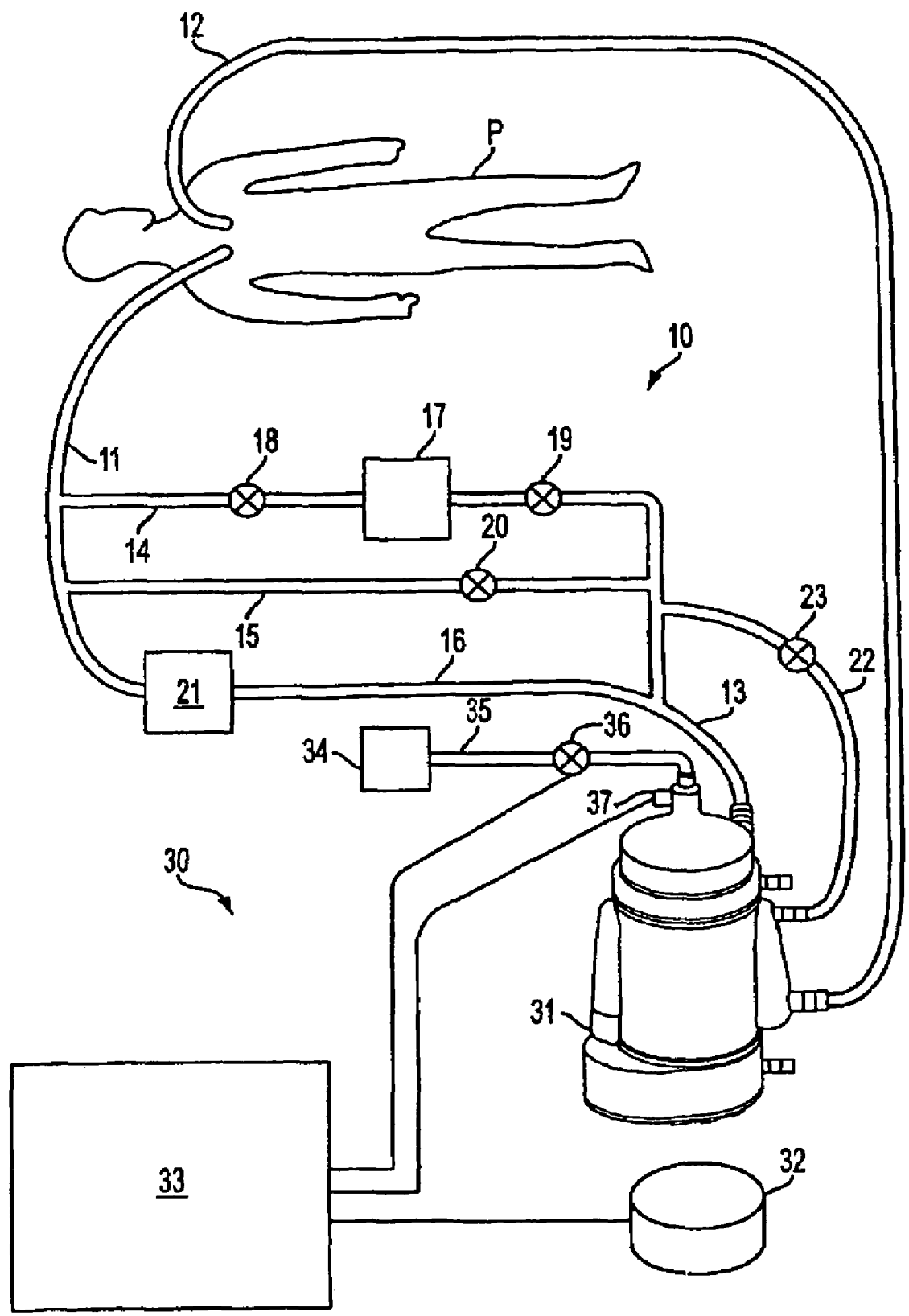
FIG. 1 is a schematic depiction of an extracorporeal blood circuit using the blood handling system of the present invention.

Referring to FIG. 1, extracorporeal blood circuit 10 including blood handling system 30 of the present invention is described. Extracorporeal blood circuit 10 is designed for maintaining a patient on full or partial bypass support, for example, during a coronary artery bypass graft procedure or mitral valve repair procedure.

Extracorporeal blood circuit 10 includes venous line 11 that carries deoxygenated blood from patient P to blood handling system 30, and arterial line 12 that returns oxygenated blood to the patient. Each of venous line 11 and arterial line 12 are coupled to the patient through a suitable cannula, which is per se known. In accordance with known methods, the venous and arterial cannulae may be positioned in any suitable vein or artery.

Venous line 11 is coupled to inlet line 13 of blood handling system 30 via lines 14, 15 and 16. Line 14 preferably includes dynamic reservoir 17 that can be selectively added and removed from the circuit using valves 18 and 19. Dynamic reservoir 17, which preferably is a flexible storage bag, permits blood to be stored or supplied to blood handling system 30 as necessary. Valves 18 and 19 control blood flow into and out of dynamic reservoir 17. One advantage of this arrangement of extracorporeal blood circuit 10 is that the pump of the blood processing component may be used to fill and evacuate the dynamic reservoir 17 during operation by simply manipulating valves 18 and 19. Alternatively, a conventional venous storage reservoir may be used instead of dynamic reservoir 17.

Line 15 includes valve 20 which may be activated to direct blood coming from the patient to either or both of lines 13 and 16. Line 16, which may include additional valving (not shown) permits additional blood processing unit 21, such as an additional filter or heat exchanger, to be included in extracorporeal blood circuit 10. Optional recirculation line 22 includes valve 23, and permits a portion of the output of blood handling system 30 to be recirculated to the input of the blood handling system, or used in administration of cardioplegia to the patient.

Blood handling system 30 includes integrated blood processing component 31 coupled to drive unit 32 and controller 33. In accordance with one aspect of the present invention, blood handling system 30 has a gas removal system including sensor 37 and valve 36 adapted to be coupled to suction source 34 via line 35. Valve 36 and sensor 37 preferably are electrically coupled to controller 33 so that controller 33 can regulate operation of valve 36 responsive to an output of sensor 37. As explained in greater detail hereinafter, the gas removal system of the present invention removes air and other gases from extracorporeal blood circuit 10 and blood processing component 21 during priming and operation of the bypass system.

Figure 2A:
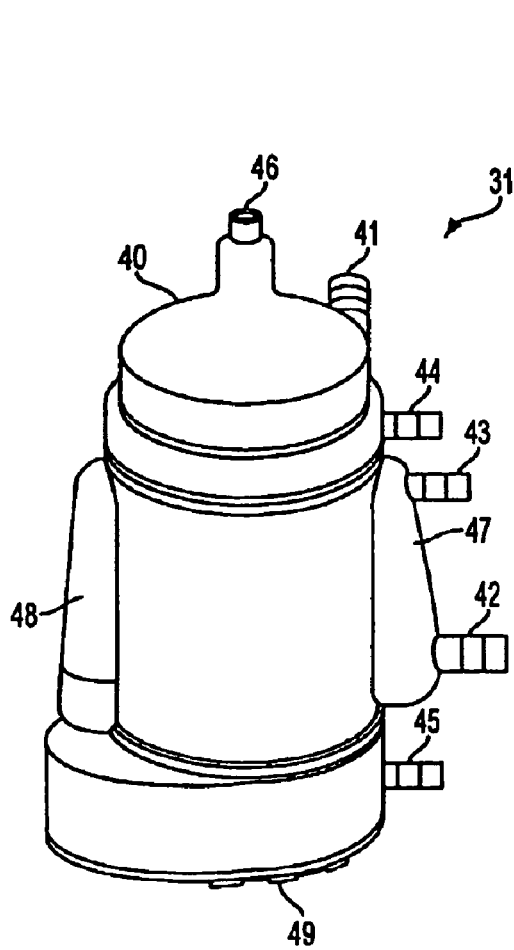
FIGS. 2A and 2B are, respectively, perspective and exploded perspective views of the integrated blood-processing component of the present invention.
Figure 2B:
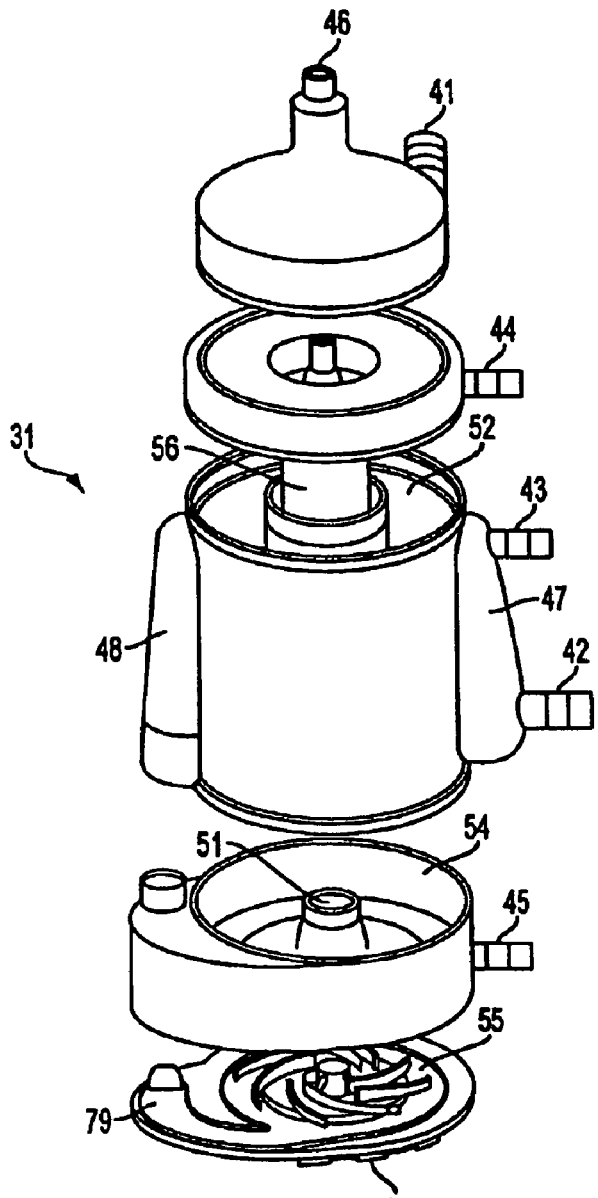
Figure 3:
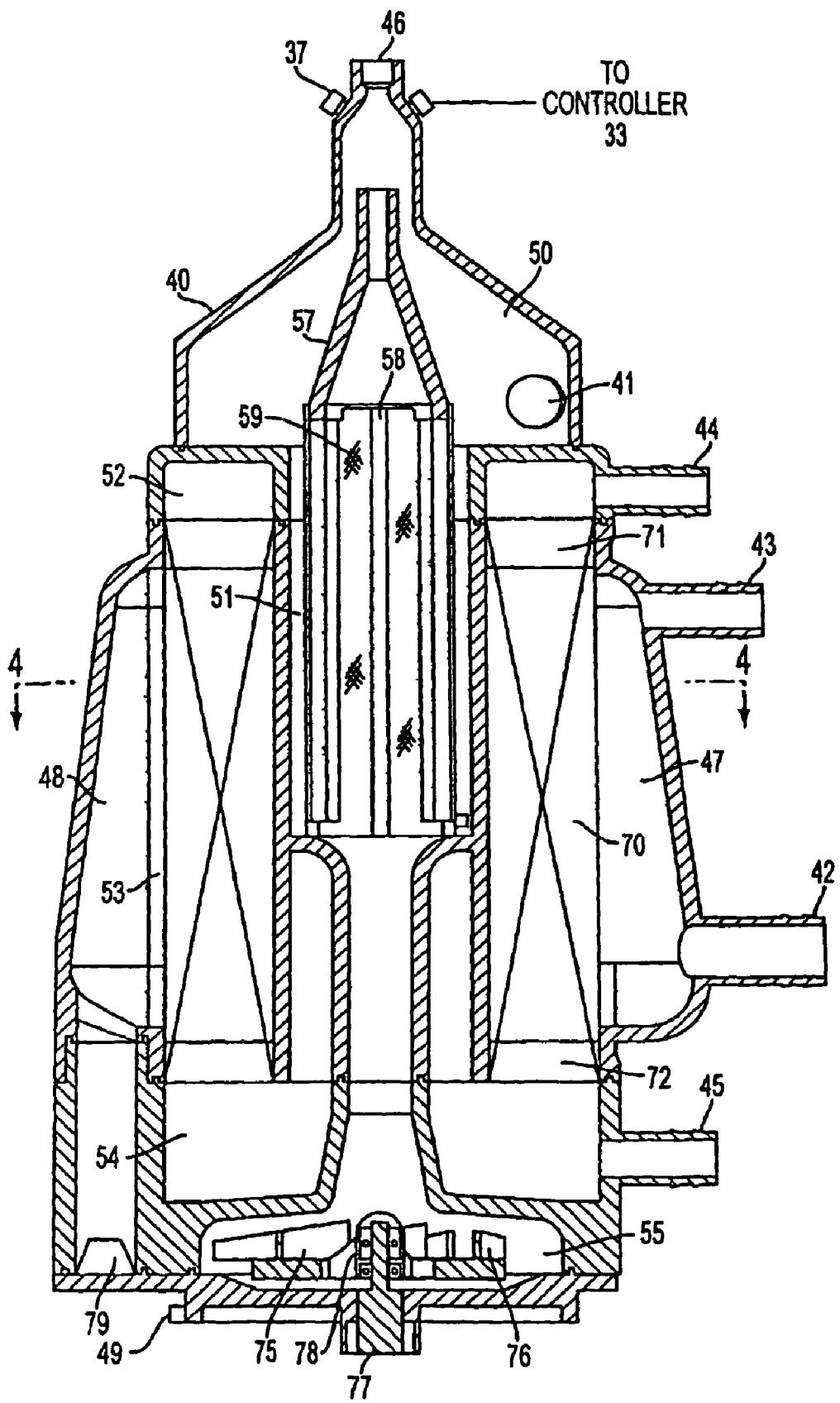
FIG. 3 is a side-sectional view of the integrated blood processing component of the present invention.

Referring now to FIGS. 2A, 2B and 3, integrated blood processing component 31 combines the features of previously known blood oxygenators, blood pumps, and blood filters into a single housing. In accordance with one aspect of the present invention, the blood handling system also provides for continuous monitoring and removal of air or other gases from the extracorporeal blood circuit during priming and operation.

Blood processing component 31 includes housing 40 having blood inlet 41, blood outlet 42, recirculation outlet 43, gas inlet port 44, gas outlet port 45 and gas removal port 46. Blood outlet 42 and recirculation outlet 43 are disposed from blood outlet manifold 47, which is disposed diametrically opposite blood inlet manifold 48 of housing 40. Blood processing component 31 preferably includes tabs 49 or other means for coupling blood processing component 31 to reusable drive unit 32.

Illustratively, housing 40 comprises a series of parts that each define a compartment: gas collection plenum 50, central void 51, upper gas plenum 52, annular fiber bundle compartment 53, lower gas plenum 54 and pump space 55. In a preferred embodiment, central void includes a larger diameter upper portion and a smaller diameter lower portion. As will of course be understand, the parts shown in exploded view in FIG. 2B could be molded or cast in more or fewer pieces.

Gas collection plenum 50 encloses a gas removal/blood filter 56 that extends within upper portion of central void 51. Gas removal/blood filter 56 causes gas entrained in blood introduced into the gas collection plenum to separate and collect in the upper portions of gas collection plenum 50. Gas removal/blood filter 56 comprises generally conical upper wall 57, baffled support structure 58 and filter material 59. Blood inlet 41 is displaced tangentially relative to the centerline of housing 40, so that blood passing through blood inlet 41 into gas collection plenum 50 swirls around upper wall 57, which is preferably fluid impermeable.

Upper wall 57 also preferably includes a chamber having a central opening through its upper surface, which communicates with the upper portion of gas collection plenum 50. This configuration allows any gas that passes through filter material 59 to escape through the opening in upper wall 57 and be evacuated from gas collection plenum 50. Advantageously, this feature facilitates rapid and easy priming of blood processing component 31, as described hereinbelow.

Filter material 59 comprises one or multiple layers of a screen-like material having an effective pore size of between 40 and 250 microns, and is mounted to baffled support structure 58. Filter material 59 serves to exclude bubbles from the blood flow by maintaining the swirling action of the blood in the central void for a sufficient time to allow the bubbles to rise to the gas collection plenum. Because the blood circulates around the outside of gas removal/blood filter 56 in central void 51, bubbles impinge against filter material 59 tangentially, and thus "bounce off." Filter material 59 preferably also forms a first stage of a progressive blood filter that is distributed throughout the blood processing component, and filters out relatively large particulate matter.

Figure 5A:
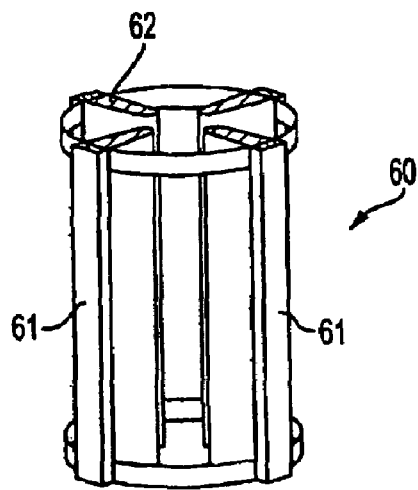
FIGS. 5A and 5B are, respectively, perspective and cross-sectional views of a gas removal/blood filter element of the gas removal system of the present invention.
Figure 5B:
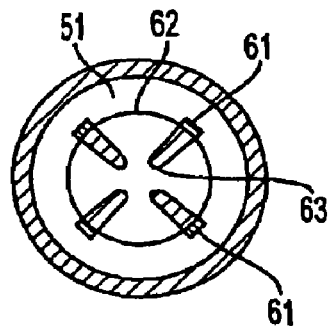
Figure 6A:
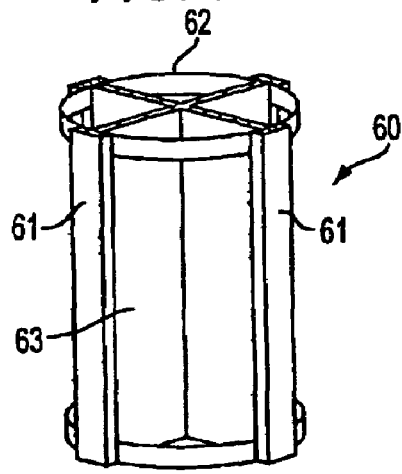
FIGS. 6A and 6B are, respectively, perspective and cross-sectional views of an alternative gas removal/blood filter element of the gas removal system of the present invention.
Figure 6B:
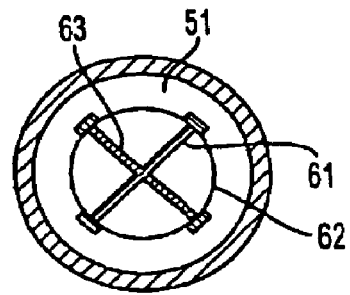

As illustrated in FIGS. 5A and 5B, support structure 58 forms an open cage 60 having longitudinal struts 61 and support rings 62. Struts 61 extend radially inward and preferably include radiused inner ends 63. Struts 61 serve as baffles to reduce swirling of blood that has passed through filter material 59. In an alternative embodiment, shown in FIGS. 6A and 6B, struts 61 are further extended radially inward to form fluid impermeable cruciform structure 63.

Referring again to FIG. 3, blood oxygenation element 70 is disposed within annular fiber bundle compartment 53, and comprises a multiplicity of gas permeable fibers arranged in an annular bundle. As is well known in the art, the gas permeable fibers are potted near the upper and lower ends of the bundle so gas may pass through the interior of the fibers via the ends of the fibers, while allowing blood to pass along the exteriors of the multiplicity of tubes in the bundle. The bundle therefore includes upper potting region 71 that separates the blood flow region within the annular bundle from upper gas plenum 52, and lower potting region 72 that separates blood flow region from the lower gas plenum 54.

Blood passing into the annular fiber bundle compartment 53 from blood inlet manifold 48 therefore flows through blood oxygenation element 70 and to blood outlet manifold 47. In accordance with one aspect of this invention, the annular fiber bundle also provides some filtration of blood passing through blood processing component 31, by filtering out particulate matter that has passed through filter material 59 employed in gas removal/blood filter 56.

The lower portion of central void 51 communicates with pump space 55, in which centrifugal impeller 75 is disposed. Impeller 75 includes a plurality of vanes 76 and is mounted on shaft 77 via bearings 78. Impeller 75 preferably comprises an injection-molded part that encloses a ferromagnetic disk, so that the disk may be magnetically coupled to drive unit 32 (see FIG. 1). Blood accelerated by impeller 75 is ejected from pump space 55 via a passageway that includes curved ramp 79. Ramp 79 serves to redirect radially outward blood flow from impeller to a longitudinal flow within blood inlet manifold 48.

In a preferred embodiment, oxygen is introduced into upper gas plenum 52 through gas inlet port 44, passes through the interiors of the multiplicity of hollow fibers in blood oxygenation element 70. Carbon dioxide, any residual oxygen, and any other gases exchanged through blood oxygenation element 70 exit into lower gas plenum 54, and are exhausted through gas outlet port 45.

In accordance with the present invention, blood processing component 31 also includes sensor 37 that monitors the level of gas or blood in gas collection plenum 50. Sensor 37 may sense a parameter indicative of a level or volume of air or other gas in gas collection plenum 50, or may simply detect the absence of blood, and may be any suitable sensor that preferably operates by a non-contact method. Suitable sensor methods include electrical-charge based, optical and acoustic methods. A resistive contact method also could be employed, in which a low electrical current is passed between adjacent electrodes only in the presence of blood.

Sensor 37 preferably is of a capacitance type, per se known in the art, that detects a change in electrical capacitance between the bulk of a liquid (in this case, blood or saline) and gas. Alternatively, sensor 37 may be optical in nature, and use a light source that has a wavelength that is minimally attenuated by blood. In this case, the light source is directed, at an oblique angle, through the blood at the top of the gas collection plenum towards a photodetector, and the sensor is positioned to detect the change in the refractive index of the blood (or saline prime) caused by the presence of air or other gases. In another alternative embodiment, sensor 37 may use an ultrasonic energy source and receiver to detect the presence of gas or absence of blood by the change in acoustic transmission characteristics.

The output of sensor 37 is supplied to controller 33 of blood handling system 30 (see FIG. 1) which in turn regulates valve 36. When sensor 37 outputs a signal indicating that gas is present in gas collection plenum, controller 33 opens valve 36, thereby coupling gas collection plenum 50 to suction source 34, such as a vacuum bottle, pump or standard operating room suction port, to evacuate the gas. Once the gas is evacuated, and the sensor detects blood at an appropriate level in gas collection plenum 50, the sensor changes its output. Correspondingly, controller 33 then closes valve 36. In this manner, gas is continuously monitored and then automatically removed from the blood by blood handling system 30.

Figure 4:
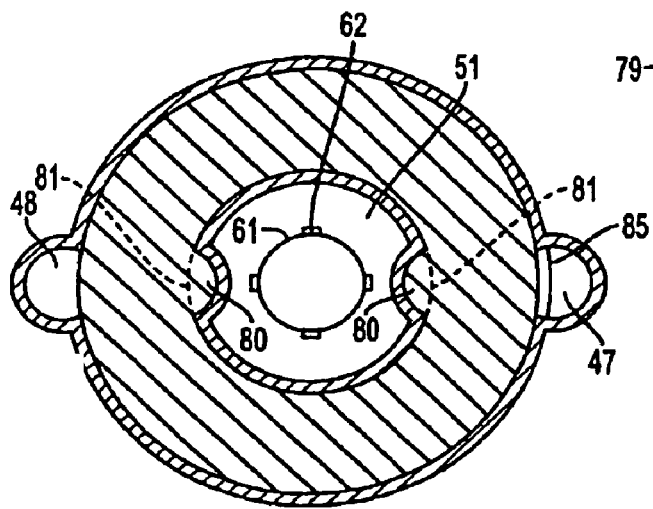
FIG. 4 is a cross-sectional view of apparatus similar to that of FIG. 3, taken along line 4-4 in FIG. 3, depicting the use of relief areas adjacent to the inlet and outlet manifolds.

Referring now to FIG. 4, additional features of the present invention are described. FIG. 4 is a cross-sectional view of apparatus similar to that of FIG. 3, but in addition includes one or more relief areas 80 that extend radially inward from blood oxygenation element 70. Relief areas 80 preferably are disposed at a radially inward portion of the blood oxygenation element 70 opposite blood inlet manifold 48 and blood outlet manifold 47. Relief areas 80 permit the annular fiber bundle to expand into the relief areas during operation, whereas the annular fiber bundle 70 occupies the position indicated by dotted lines 81 prior to operation.

In addition, in accordance with the progressive filtration aspect of the present invention, filter material 85 may be disposed between the annular fiber bundle and the entrance to blood outlet manifold 47. Filter element 85 provides an additional third stage of filtration for blood passing through blood processing component 31, and preferably comprises a screen-like material having the same or smaller effective pore size than the filter material included in gas removal/blood filter 56. Because blood has already passed through two stages of filtration before reaching filter element 85 (i.e., gas removal/blood filter 56 and the fibers of blood oxygenation element 70), it is expected that this filter will be capable of sustaining extended use without clogging.

In operation, deoxygenated blood from patient P is routed through one or more lines 14-16 to blood inlet 41 of blood processing component 31. Blood entering gas collection plenum 50 is induced to circulate around the exterior of gas removal/blood filter 56 until air or other gases entrapped in the blood separate out of the blood and collect in the upper portion of the gas collection plenum. Responsive to the detection of the presence of a predetermined level or volume of gas by sensor 37, controller 33 controls operation of valve 36 to evacuate the gas.

Applicant has observed in prototype designs that the gas removal system of the present invention is capable of removing large amounts of air from the extracorporeal blood circuit during initial startup, thereby greatly reducing the amount of saline or donor blood required to prime the system. Advantageously, this feature facilitates rapid and easy set-up of the blood handling system, as well as reduces the amount of saline or donor blood delivered to the patient.

As blood circulates around gas removal/blood filter 56 in central void 51, it is drawn by the negative pressure head created by impeller 75 through filter material 59 and down through central void 51 into pump space 55. Rotation of impeller 75 caused by drive unit 32, under the control of controller 33, propels blood up curved ramp 79 into blood inlet manifold 48.

From blood inlet manifold 48, the blood traverses blood oxygenation element 70 where it exchanges carbon dioxide and other gases for oxygen. Oxygenated blood then passes through filter element 85, if present (see FIG. 4), and into blood outlet manifold 47. Oxygenated blood then is directed back to the patient through arterial line 12, or optionally, a portion of the oxygenated blood may be recirculated through line 22.

While blood handling system 30 of the present invention thus is used in substantially the same manner as previously known blood handling equipment, it does provide a number of advantages over previously known blood handing equipment. First, the system is simple to use, with integrated blood processing component 31 embodying a number of blood handling features. Thus, for example, the clinician is not required to connect together a pump, oxygenator, or blood filter, thereby saving time, space and priming volume.

Blood processing component 31 advantageously may serve as a progressive, distributed, blood filter that provides staged filtration of the blood flow. Specifically, gas removal/blood filter 56 serves as a first filter stage to filter out matter having a size of 40-250 microns, the fibers of blood oxygenation element 70 serve as a second filter stage to filter out particulate matter having a size of approximately 100 microns and larger, and filter element 85, if present at the entrance to the blood outlet manifold 47, provides a third filter stage that filters out material having a size of 40 microns or larger.

Another advantage of the system of the present invention is that the gas removal system facilitates priming of the system with significantly less saline or donor blood. As is conventional, before initiating bypass support, the entire system must be primed with blood to purge all air out of the system. When priming the system of the present invention, however, the patient's own blood pressure may be used to fill venous lines 11, 14-16 and blood processing component 31. Advantageously, the gas removal system may be used to actively remove air and draw blood into the blood processing component.

In particular, when the gas removal system is turned on, sensor 37 will detect gas in the gas collection plenum 50 and will then actively remove the gas as described hereinabove. In this manner, extracorporeal circuit 10 can be primed by operation of the gas removal system. Once blood processing component 31 has been thus primed, drive unit 32 may be activated, so that impeller 75 also may be operated together with the gas removal system to purge air from the circuit. Blood may be recirculated through line 22 and valve 23 until all air has been purged from the system.

Yet another advantage of the system of the present invention is that additional blood processing elements 21 may be added to the system during operation, with the gas removal system priming the newly added device during operation. When such an element 21 is added to the system during operation, line 16 is temporarily clamped to isolate the location for new element 21. Blood processing element 21 then is connected, unprimed, in line 16. The clamps then are opened, so that any air in new element 21 is removed automatically by the gas removal system. The gas removal system of the present invention therefore may be used to remove air while delivering blood to the patient or when simply circulating the blood through line 22 until it is confirmed that all air from new element 21 has been removed.

Figure 7:
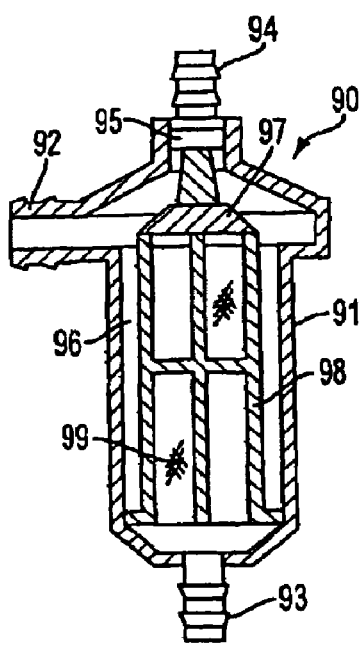
FIG. 7 is a cross-sectional view of a gas removal/blood filter of the gas removal system of the present invention configured for use in previously known extracorporeal blood processing systems.

Referring now to FIG. 7, gas removal element 90 constructed for use in a stand-alone gas removal system in accordance with the present invention is described. Gas removal element 90 is intended for use with previously known extracorporeal bypass systems to provide some of the advantages described hereinabove.

Gas removal element 90 includes transparent housing 91 having blood inlet 92, blood outlet 93, gas removal port 94, and sensor 95. Housing 91 encloses gas removal/blood filter 96, which in turn comprises generally conical upper wall 97, support structure 98 and filter material 99. Upper wall 97, support structure 98 and filter material 99 may be constructed as described with respect to the embodiments of FIG. 5 or 6 set forth hereinabove. When used in conjunction with a suction source and suitable controller, gas removal element may be used to remove air or other gases entrained in the blood in the venous line, as well as to facilitate priming.

Figure 8:
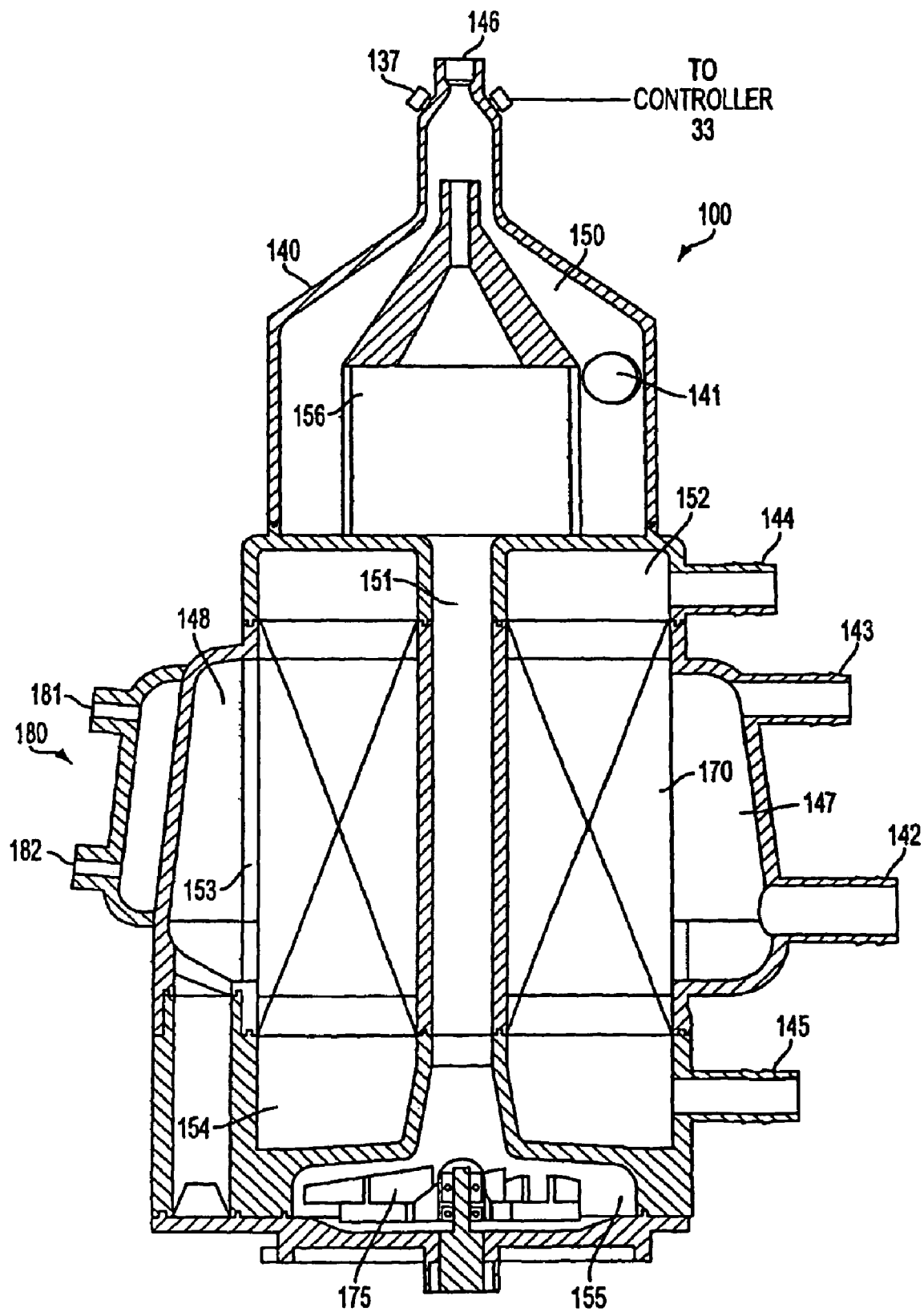
FIG. 8 is a side-sectional view of alternative embodiment of the integrated blood processing component of the present invention.

Referring to FIG. 8, an alternative embodiment of the blood processing component of the present invention is described. In FIG. 8, like components of the embodiment of FIG. 3 are indicated by reference numerals increased by 100. Thus, blood processing component 100 comprises housing 140 having sensor 137, blood inlet 141, blood outlet 142, recirculation outlet 143, gas inlet port 144, gas outlet port 145, gas removal port 146, blood outlet manifold 147, blood inlet manifold 148, gas collection plenum 150, central void 151, upper gas plenum 152, annular fiber bundle compartment 153, lower gas plenum 154 and pump space 155. Gas removal/blood filter 156 is disposed in gas collection plenum 150, blood oxygenation element 170 is disposed in annular fiber bundle compartment 153, and impeller 175 is rotatably fixed in pump space 155.

Blood processing component 100 differs from the embodiment of FIG. 3 in that: (1) gas removal/blood filter 156 is positioned entirely in gas collection plenum 150 and does not extend into central void 151; (2) blood oxygenation element 170 is shorter and wider than blood oxygenation element 70; and (3) heat exchanger 180 is disposed on blood inlet manifold 148.

Heat exchanger 180 includes inlet port 181 and outlet port 182, and enables heated or cooled liquid, such as water, to contact the blood inlet manifold and thereby heat or cool the blood flowing therethrough. Heat exchanger 180 also may have tubes, fins or the like to enhance heat transfer, and may be positioned at any other suitable location, such as adjacent to impeller 175. Alternatively, heat exchanger 180 may use any other suitable heat exchange structure, such as a resistive heater element disposed within pump space 155.

In addition, in the embodiment of FIG. 8, gas removal/blood filter 156 comprises a pleated structure, rather a screen-like filter material. Operation of blood processing component 100 is as described above with respect to the embodiment of FIG. 3, except that in addition the blood temperature may be altered as desired for a particular application.

Referring now to FIGS. 9 and 10, further details of the centrifugal pump employed in the blood processing component of the present invention are described. Centrifugal pump 200 includes impeller 201 having a plurality of arcuate vanes 202 integrally formed with disk 203. Shaft 204 includes lower portion 205 that is press fit or adhesive bonded into the bottom of housing 40 (see FIG. 3.), and upper portion 206 that accepts seal 207, bearings 208 and sleeve 209. Sleeve 209 is press fit or adhesive bonded to the interior of a bore in hub 210 of impeller 201. Seal 207 prevents blood from entering bearings 207.

As shown in FIG. 10, impeller 201 preferably comprises an injection moldable plastic, such as polycarbonate, and is case in two sections. A first section includes lower portion 211 of disk 203 and hub 210, and includes a recess that accepts a ferromagnetic washer 212. In accordance with another aspect of the present invention, washer 212 includes through holes 213, which permit the injection process to be completed. Holes 213 also serve to define magnetic poles in the washer, that permit the impeller to become magnetically coupled to permanent magnets, or electromagnets, employed in drive unit 32.

During a second step of the injection molding process, first section 211 is placed in a suitable mold, and the remainder of impeller 201 (illustratively shown at 214) is formed by injecting material into the mold through holes 213 in the first section and washer 212. When fully molded, washer 212 is completely encased in the plastic, to prevent undesirable blood-metal interaction.

Figure 11A:
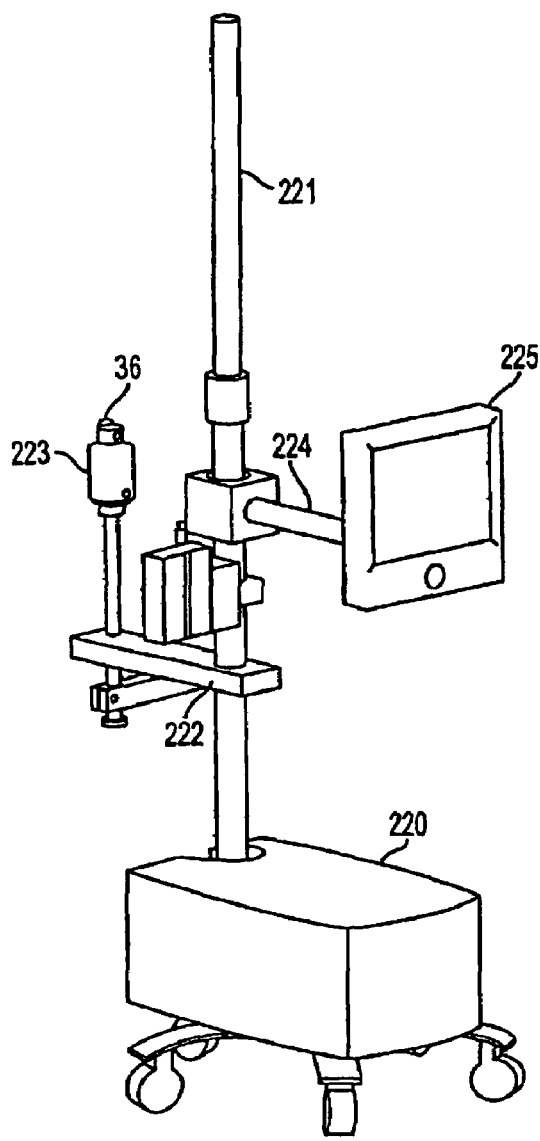
FIGS. 11A and 11B are front and rear perspective views of the blood handling system of the present invention.
Figure 11B:
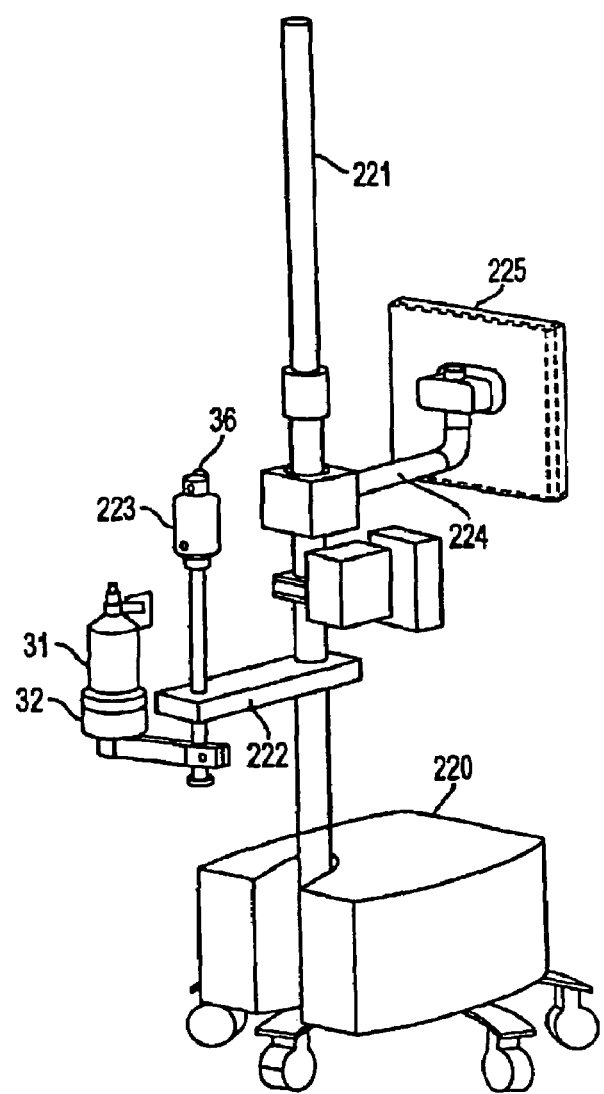

FIGS. 11A and 11B depict an illustrative embodiment of the blood handling system of the present invention. In this embodiment, from which all blood, gas and electrical lines have been omitted for clarity, microprocessor-driven controller 33 (see FIG. 1) and a back-up battery are enclosed in wheeled base 220. Pole 221 is mounted in base 220, and includes support arm 222 that supports blood processing component 31 on drive unit 32. Support arm 222 also carries solenoid 223 that controls valve 36, which is in turn coupled to a suction source, such as the hospital wall suction port found in most operating rooms. Pole 221 also carries support arm 224, which carries display screen 225. Screen 225 preferably is a touch-sensitive screen coupled to the controller, and serves as both an input device for the blood handling system and a display of system function.

Figures 12A, 12B:
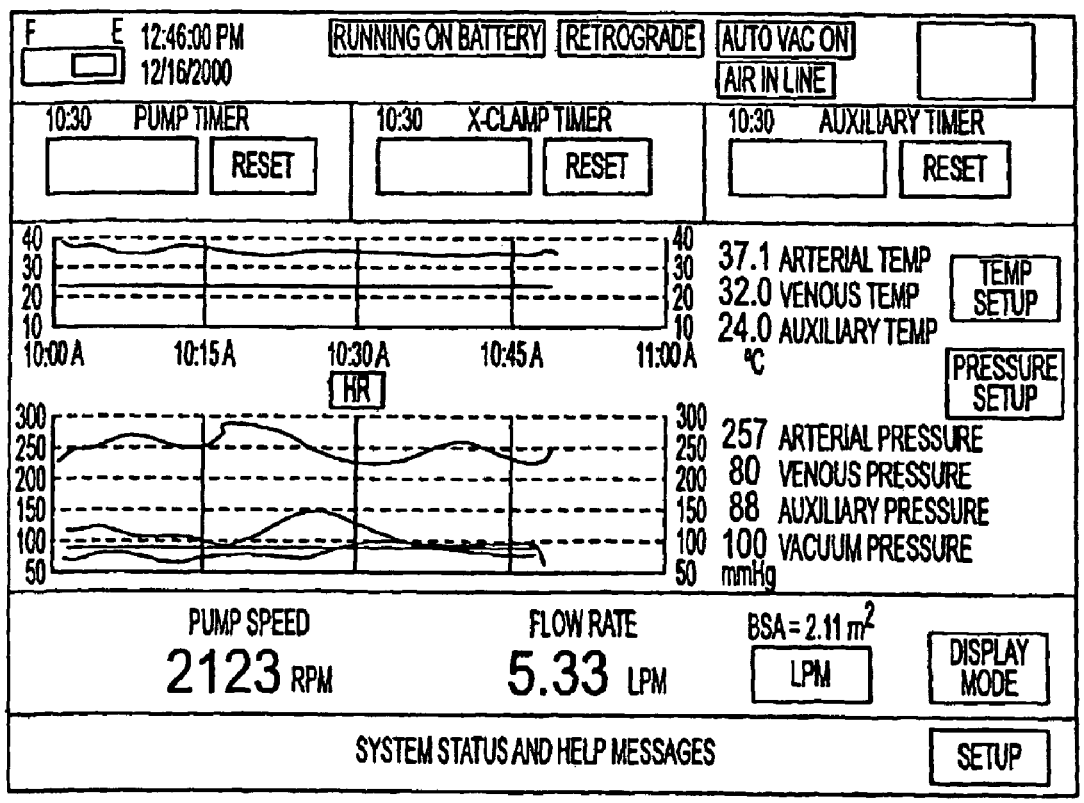
FIGS. 12A and 12B are representative screens depicting the display of parameters monitored and/or controlled by the blood processing system of the present invention.

FIGS. 12A and 12B provide representative samples of the information displayed on the main windows of the blood handling system. As will of course be understood by one of ordinary skill in the art of computer-controlled equipment, the software used to program operation of the controller may include a number of set-up screens to adjust particular system parameters. FIGS. 12A and 12B are therefore the windows that will most commonly be displayed by the clinician during a procedure.

The display of FIG. 12A, includes an indicator of battery status, a series of timers for pump operation, duration of cross-clamping, and an auxiliary timer, arterial and venous temperatures and pressures, as measured, for example, at the blood inlet and blood outlet of the blood processing component, the speed of the centrifugal pump and the corresponding blood flow rate. Preferably, the controller is programmed with a number of algorithms for determining an appropriate blood flow rate during the procedure, as determined based on body surface area (BSA). The window also may display the value of BSA determined by the selected algorithm based on the patient's dimensions, and the suggested blood flow rate.

The display of FIG. 12B includes much of the same information provided in the window of FIG. 12A, but in addition may display temperatures and pressures graphically as well as numerically, so that the clinician can quickly identify trends in the data and take appropriate corrective measures. In addition, a lower portion of the windows displayed in FIGS. 12A and 12B may present system status or help messages, and include touch sensitive buttons that permit to access the other available functions.

Although preferred illustrative embodiments of the present invention are described above, it will be evident to one skilled in the art that various changes and modifications may be made without departing from the invention. It is intended in the appended claims to cover all such changes and modifications that fall within the true spirit and scope of the invention.

What is claimed is:

1. Apparatus for use in conjunction with a blood pump for degassing blood, the apparatus comprising:
    a venous line configured to be coupled to a patient;
    an outlet line configured to be coupled to the pump;
    a gas removal system interposed between the venous line and the outlet line, the gas removal system comprising a rigid housing having a substantially circular portion disposed beneath and in communication with a frustoconical gas collection plenum including a gas removal port, a filter element having a blood-impermeable upper wall disposed within the housing, and a blood inlet port configured so that venous blood entering the housing swirls around the upper wall before passing through the filter element, the gas removal system coupled directly to the pump so that the pump induces a negative pressure in the gas removal system and the venous line to draw blood through the blood inlet port;
    a sensor disposed on the gas collection plenum to monitor a level of gas or blood in the gas collection plenum;
    a suction line coupled to the gas removal port;
    a valve operatively associated with the suction line;
    a microprocessor-based controller coupled to the sensor to continuously monitor the level of gas or blood in the gas collection plenum, the controller programmed to selectively actuate the valve to remove gas accumulated in the gas collection plenum.

2. The apparatus of claim 1 further comprising at least a first pole-mounted support arm for supporting the gas removal system and the pump.

3. The apparatus of claim 2 further comprising at least a second pole-mounted support arm for supporting the control panel.

4. The apparatus of claim 1 wherein the sensor comprises an ultrasonic sensor.

5. The apparatus of claim 1 wherein the sensor comprises a capacitive sensor.

6. The apparatus of claim 1 wherein the gas removal system and pump are coupled together in a fixed, predetermined arrangement.

7. The apparatus of claim 1 wherein the filter element comprises a first stage of a multi-stage blood filter.

8. The apparatus of claim 1 further comprising a recirculation line coupled between the outlet line and the gas removal system.

9. The apparatus of claim 1 wherein the pump comprises an impeller that is magnetically coupled to a reusable drive unit.

10. The apparatus of claim 1, wherein the valve comprises a solenoid-driven valve.

* * * * *